United States Patent [19]

Khuddus

[11] Patent Number: 5,049,601
[45] Date of Patent: Sep. 17, 1991

[54] HALOGENATED BIS-IMIDE FLAME RETARDANTS

[75] Inventor: Mo A. Khuddus, Baton Rouge, La.

[73] Assignee: Ethyl Corporation, Richmond, Va.

[21] Appl. No.: 385,235

[22] Filed: Jul. 24, 1989

Related U.S. Application Data

[62] Division of Ser. No. 150,753, Feb. 1, 1988, Pat. No. 4,871,863.

[51] Int. Cl.$^5$ .................. C08K 5/34; C07D 207/44
[52] U.S. Cl. ............................... 524/94; 252/401; 548/461; 548/462
[58] Field of Search ............... 524/94; 252/401; 548/461, 462

[56] References Cited

U.S. PATENT DOCUMENTS

| | | | |
|---|---|---|---|
| 3,868,388 | 2/1975 | Dotson, Jr. et al. | 548/462 |
| 3,966,726 | 6/1976 | Toth et al. | 260/249.8 |
| 4,092,345 | 5/1978 | Wolford et al. | 252/8.1 |
| 4,125,535 | 11/1978 | Wolford | 548/462 |
| 4,374,220 | 2/1983 | Sonnenberg | 524/94 |
| 4,535,170 | 8/1985 | Sonnenberg | 548/462 |
| 4,581,396 | 4/1986 | Sonnenberg | 524/87 |

FOREIGN PATENT DOCUMENTS 0023420 10/1983 European Pat. Off. .
2926638 1/1981 Fed. Rep. of Germany .

Primary Examiner—Kriellion S. Morgan
Attorney, Agent, or Firm—Edgar E. Spielman, Jr.

[57] ABSTRACT

This invention relates to a process for enhancing the properties of alkylene($C_1$–$C_6$)-bis-(tetrabromophthalimide) or bis-(tetrabromophthalimide) produced by the bromination, respectively, of alkylene($C_1$–$C_6$)-bis-(phthalimide) or bis-(phthalimide) with a brominating agent in the presence of oleum, the process comprising curing the alkylene($C_1$–$C_6$)bis-(tetrabromophthalimide) or bis-(tetrabromophthalimide) at a temperature above about 150° C. and below the melting point of the tetrabromophthalimide being cured for a period of from about 36 hours to about 5 hours. This enhanced product and its use in molding and extrusion compositions and in molded and extruded articles is also disclosed.

26 Claims, No Drawings

HALOGENATED BIS-IMIDE FLAME RETARDANTS

This application is a division of application Ser. No. 150,753, filed Feb. 1, 1988, now U.S. Pat. No. 4,871,863.

BACKGROUND OF THE INVENTION

This invention relates to improved halogenated bis-imide flame retardants, to their manufacture and to compositions containing a flammable material and such halogenated bis-imides.

As is taught in U.S. Pat. No. 4,374,220, there are a multitude of halogenated bis-imides which are effective as flame retardants in composition with macromolecular flammable materials, e.g. polymers. These compositions are useful in making articles such as wire insulation coverings and electronic housings. Of these halogenated bis-imides, the alkylene($C_1$-$C_{66}$)-(tetrabromophthalimide)s are especially commercially significant.

A presently used commercial route for producing alkylene ($C_1$-$C_6$)-bis-(tetrabromophthalimide)s comprises reacting tetrabromophthalic anhydride with a diaminoalkane in the presence of water and an alkanoic acid to yield an alkylene-diammonium-bis-tetrabromophthalate). The reaction mass is then heated to about 210° C. for a period of about 8 hours and the resultant desired alkylene($C_1$-$C_6$)-bis-(tetrabromophthalimide) product is recovered therefrom. This product is particularly useful as it has good thermal stability and resistance to UV degradation. However, the product has a yellow color which argues against its presence in compositions used for forming white articles. Also, the intensity of the yellow color can vary between product batches, which color variance makes it difficult for the article manufacturer to maintain consistency in the color of the articles produced. To overcome the yellow color problem, the art has provided processes which produce a white alkylene($C_1$-$C_6$)-bis-(tetrabromophthalimide).

U.S. Pat. No. 4,125,535 discloses a process for producing white alkylene($C_1$-$C_6$)-bis-(tetrabromophthalimide) by reacting tetrabromophthalic anhydride with diaminoalkane in a solvent system comprised of a liquid aromatic hydrocarbon and an alkanoic or aralkanoic acid.

Another process for producing this white bis-imide is disclosed in European Patent No. 0 023 420. This process comprises the bromination of alkylene($C_1$-$C_6$)-bis-(phthalimide) with a brominating agent, e.g. bromine, in 40–80% oleum. The product is white, however, it is not as thermally stable or as resistent to UV degradation as is the case for the before-described yellow alkylene($C_1$-$C_6$)-bis-(tetrabromophthalimide). Also it has now been demonstrated, that when compositions containing this white bis-imide are compression molded to form articles, the resultant article can be discolored by a yellow color or tint. This discoloration is believed to be due to a yellowing of this bis-imide as a result of its being exposed to the compression molding process conditions. Since injection molding processes are usually run under process conditions which are more harsh than those used in compression molding, it is expected, for this bis-imide, that the yellowing problem which would be encountered in injection molding would be at least as severe as that encountered in compression molding.

It is, therefore, an object of this invention to provide a white bis-imide, i.e. alkylene($C_1$-$C_6$)-bis-(tetrabromophthalimide) or bis-(tetrabromophthalimide), which has high thermal stability, resistance to UV degradation and which does not significantly contribute a yellow color to an article made from a composition containing such bis-imide.

It is also an object of this invention to provide a process for producing such a white bis-imide.

It is also an object of this invention to provide a composition which contains a macromolecular flammable constituent and a white bis-imide of the invention wherein the color of the composition is not significantly affected by a yellow color contribution from the bis-imide during the processing of the composition to form an article.

These and other objects are attained by oven curing alkylene($C_1$-$C_6$)-bis-(tetrabromophthalimide) or bis-(tetrabromophthalimide) which have been produced, respectively, by the bromination of alkylene($C_1$-$C_6$)-bis-(phthalimide) or bis-(phthalimide) with a brominating agent in the presence of oleum.

THE INVENTION

For the purposes of this disclosure, the alkylene($C_1$-$C_6$)-bis-(phthalimide)s and the bis-(phthalimide) referred to herein are represented by the formula,

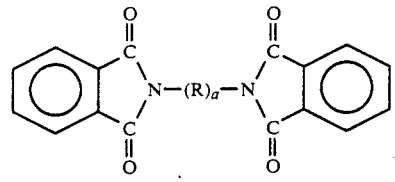

wherein R is a divalent alkylene radical containing 1 to 6 carbon atoms and a is 1 or 0. R can be a branched or be a straight chain radical. R is preferably methylene(—$CH_2$—) or ethylene(—$CH_2CH_2$—). When a is 0, the bonding between the two phthalimide groups is by way of a N—N bond.

The alkylene($C_1$-$C_6$)-bis-(tetrabromophthalimide)s and the bis-(tetrabromophthalimide)s referred to herein are represented by the formula,

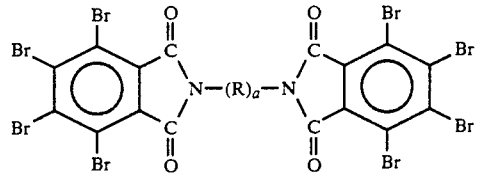

wherein R and a are as recited above.

The oleum route, as before noted, to a white alkylene-($C_1$-$C_6$)-bis-(tetrabromophthalimide) comprises the bromination of alkylene($C_1$-$C_6$)-bis-(phthalimide) with a brominating agent in the presence of oleum.

The brominating agent used is usually bromine, although other brominating agents, such as bromine chloride, can be employed if desired. The amount of bromine used should be at least the amount theoretically required to achieve complete bromination of the aromatic rings of the starting material, i.e., an amount that provides one bromine atom for each available aromatic carbon atom. There is no maximum to the amount of bromine that can be used, but there is no advantage in using unnecessarily large amounts of bromine. Therefore, it is preferable to employ amounts of bromine that provide from about 1 to about 1.5, most preferably from about 1.05 to about 1.15, atoms of bromine per available aromatic carbon atom. Excellent results are obtained by using bromine in an amount that is about 12-14% more than the amount theoretically required for complete bromination.

The oleum used is a solution of 40-80% by weight of sulfur trioxide in concentrated sulfuric acid. Because of its ready availability and its effectiveness, a 60-70% oleum is preferred. The oleum is employed in an amount which provides at least one molecule of sulfur trioxide per available aromatic carbon atom and is preferably used in larger amounts since the reaction rate increases with an increased concentration of sulfur trioxide in the reaction mixture. Ordinarily the oleum is utilized in an amount which provides from about 1 to about 1.9, preferably from about 1.25 to about 1.75, molecules of sulfur trioxide per available aromatic carbon atom. Thus, it is preferable to use from about 8 to about 15 mols, most preferably from about 10 to about 14 mols, of sulfur trioxide per mol of alkylene($C_1$-$C_6$)-bis(phthalimide). Excellent results are obtained by using about 50% more sulfur trioxide than is theoretically required for complete sulfonation of the aromatic rings of the bis-imide reactant. When an oleum containing the desired amount of sulfur trioxide is not readily available, the desired concentration of sulfur trioxide can be attained by introducing sulfur trioxide to a sulfur trioxide deficient system.

In the reaction, relatively mild conditions are suitable. It is not necessary to use high temperatures or pressures. Ordinarily the desired bromnation can be achieved by heating the reactants to a temperature of from about 35 to about 60° C., preferably about 55° C., for at least about 3 hours, although it is sometimes desirable to use higher temperatures, e.g. about 70-90° C., to complete the bromination when the concentration of sulfur trioxide in the reaction mixture is relatively low during the initial stage of the reaction. Such relatively low concentrations in the reaction mixture may occur, for example, if a whole charge of alkylene($C_1C_6$)-bis-(phthalimide) is initially present, as distinguished from being added gradually to the oleum.

The reaction may be conducted under atmospheric or superatmospheric pressure, with or without a catalyst. When pressure is employed, it is ordinarily only the slight pressure created by a back pressure device, although higher pressures may be used if desired. When a catalyst is employed, it may be any suitable bromination catalyst, e.g., sodium nitrate, nitrogen dioxide, aluminum, iron, an iron-iodine mixture, a silver catalyst, etc. Catalyst, when employed, are normally used in concentrations of about 0.1-2%, based on the weight of the alkylene($C_1$-$C_6$)-bis-(phthalimide). Particularly good results are obtained when the catalyst is a 50:50 mixture of iron and iodine, and even better results are obtained when the catalyst is a silver catalyst, e.g., silver or any inorganic or organometallic silver compound capable of catalyzing the bromination of aromatic carbons. Because of availability as well as effectiveness, the preferred silver catalysts are silver, silver nitrate, silver sulfate, silver carbonate, silver acetate, silver chloride, silver bromide, and mixtures thereof. Silver nitrate is particularly preferred.

The manner of admixing the reactants is not critical, although the reaction is much more efficient when the reactants are admixed in such a manner to maximize the concentration of sulfur trioxide at all times. One suitable method of conducting the reaction is to dissolve the alkylene($C_1$-$C_6$)-bis-(phthalimide) and optional catalyst in the oleum, to heat the solution to about 35-60° C., to add the brominating agent thereto over a period of about 3-10 hours, to maintain the reaction mixture at about 35-60° C. for an additional 0-5 hours, to raise the reaction temperature to about 70-90° C., and to maintain the reaction mixture at about 70-90° C. for about 1-3 hours.

A preferred method of conducting the reaction is to charge optional catalyst and about 45-75% of the oleum to a reaction vessel, to heat the oleum and optional catalyst to about 35-60° C., and to simultaneously add the bromine and a solution of the alkylene($C_1$-$C_6$)-bis-(phthalimide) in the remainder of the oleum over a period of about 3-5 hours.

When the bromination has been completed, the alkylene($C_1$-$C_6$)-bis-(tetrabromophthalimide) product is recovered by conventional techniques. Conveniently the product is isolated by raising the temperature of the reaction mass to about 100-140° C. to distill off the excess bromine and sulfur trioxide. The reaction mass is then cooled to room temperature and filtered. The recovered precipitate, i.e. alkylene($C_1$-$C_6$)-bis-(tetrabromophthalimide), is washed with water until it is free of acid and then dried. The drying is generally accomplished by heating the washed precipitate to about 125° C. for several hours.

The production of white bis-(tetrabromophthalimide) is effected in a manner similar to that recited above for alkylene ($C_1$-$C_6$)-bis-(tetrabromophthalimide) except that bis-(phthalimide) intermediate is used in place of the alkylene($C_1$-$C_6$)-bis-(phthalimide) intermediate.

The so formed and recovered white alkylene($C_1$-$C_6$)-bis-(tetrabromophthalimide) product has, as before stated, a thermal stability and resistance to UV degradation which is inferior to that of the yellow alkylene($C_1$-$C_6$)-bis-(tetrabromophthalimide) product produced by the reaction of tetrabromophthalic anhydride and diaminoalkane. To enhance the white products of this invention so that they are substantially equivalent to the yellow product, in regards to thermal stability and resistance to UV degradation, it has now been found that a further process step is useful. In accordance with this invention, this enhancement is accomplished by curing the white alkylene($C_1$-$C_6$)-bis-(tetrabromophthalimide) or bis-(tetrabromophthalimide) product at a temperature above about 150° C. and below the melting point of the tetrabromophthalimide, i.e. the alkylene ($C_1$-$C_6$)-bis-tetrabromophthalimide or the bis-tetrabromophthalimide being cured, for a period within the range of from about 36 hours to about 5 hours. Generally, the white bis-imides of this invention can be cured at a temperature of from about 150° C. to 300° C. without melting. The longer curing periods are associated with the lower curing temperatures and the shorter curing periods are associated with the higher curing temperatures. Preferably, the curing temperature is within the range of from about 180° C. to about 250° C. with a correspondent curing period within the range of from about 10 hours to about 6 hours. A most highly preferred curing temperature will be within the range of from about 220° C. to about 250° C. in association with a curing period within the range of from about 8 to about 6 hours. The curing period can be longer than those specified above for a certain temperature, and such periods have been used. However, no particular benefit is gained in using excessively long curing periods. The curing can be effected with any conventional technique and apparatus, provided that, the technique and apparatus chosen assured uniform curing and does not deleteriously degrade or contaminate the product being cured. The curing can occur at subatmospheric, atmospheric or at superatmospheric pressures dependent upon the technique and apparatus used. An especially useful technique is oven curing in which a hot forced air oven is used. The product is best cured by being placed in the oven in thin layers, e.g. 0.25 in. to 4 in., to insure uniform curing. The specification of layer thickness is not critical so long as uniform curing is obtained.

The cured white alkylene($C_1$–$C_6$)-bis-(tetrabromophthalimide) or bis-(tetrabromophthalimide) (hereinafter referred to as cured white bis-imide) not only has good thermal stability and resistance to UV degradation but also has a lower acid number, less than about 2, and a higher bromine content, within the range of from about 63% to about 69%, than is the case for the precursor uncured white alkylene($C_1$–$C_6$)-bis-(tetrabromophthalimide and bis-(tetrabromophthalimide) (hereinafter referred to as uncured white bis-imide). Indeed, for cured ethylene-bis-(tetrabromophthalimide) an acid number within the range of from about 0.15 to about 1.0 and a bromine content within the range of from about 65% to about 67% are obtainable. A preferred acid number range for this cured white bis-imide is from about 0.15 to about 0.9.

The cured white bis-imides of this invention function as flame retardants when compounded with macromolecular flammable materials. The compositions so formed can additionally contain other conventional additives such as stabilizers, processing aids and the like.

It will be apparent to those skilled in the art that for all cases no single precise value for the proportion of the cured white bis-imide in the composition can be given, since this proportion will vary with the particular flammable material, the presence of other additives, the particular cured white bis-imide used, and the degree of flame retarding sought in any given application. Further, the proportion necessary to achieve a given extent of flame retardance in a particular composition will depend upon the shape of the article into which the composition is to be made, for example, electrical insulation, tubing and film will each behave differently. In general, however, the composition may contain from about 5% to about 40%, preferably 10% to 30%, of the cured white bis-imide when the cured white bis-imide is the only flame retardant compound in the composition.

It will be appreciated that one or more bis-imides, be they the cured white bis-imides of this invention or be they a mix of cured and uncured white bis-imides, may be incorporated in the same composition and that other flame retardant materials may be used in conjunction with the bis-imides. (Note, however, that the use of uncured white bis-imides may create color and degradation problems if present in substantial amounts.) It is especially advantageous to use the cured white bis-imide and an inorganic compound, especially the oxide, of a Group V element, for example, bismuth, arsenic, phosphorus and especially antimony, in a composition. Of these compounds, antimony oxide is especially preferred. If such a compound is present in a composition, the quantity of total bis-imide, be it all cured or a mix of cured and uncured, needed to achieve a given flame-retardance is accordingly reduced.

The compositions containing the total bis-imide/inorganic compound flame retardant system may contain up to about 40% by weight of the system, preferably between 20% and 30% by weight. It is believed that the inorganic compound and the total bis-imide will react under the conditions of combustion of a flammable material to form inorganic bromine compounds, e.g., bromine and oxybromides, which assist in retarding combustion. The bromine-bearing bis-imide also acts as a flame retardant independently and the proportions in a flame retardant system are a matter of choice, depending, inter alia, on the material in which the system is to be incorporated and commercial considerations. Generally, the total bis-imide and the inorganic compound are in a weight ratio of from about 1:1 to about 7:1, and preferably of from about 2:1 to about 4:1.

The cured white bis-imides and flame retardant systems containing cured white bis-imides may be used in combination with virtually any flammable material. The material may be macromolecular, for example, a cellulosic material or a polymer. Illustrative polymers are: olefin polymers, cross-linked and otherwise, for example, homopolymers of ethylene, propylene, and butylene; copolymers of two or more of such alkylene monomers and copolymers of one or more of such alkylene monomers and any other copolymerizable monomers, for example, ethylene/propylene copolymers, ethylene/ethyl acrylate copolymers and ethylene/vinyl acetate copolymers; polymers of olefinically unsaturated monomers, for example, polystyrene, e.g. high impact polystyrene, and styrene copolymers; polyurethanes; polyamides; polyimides; polycarbonates; polyethers; acrylic resins; polyesters, especially poly(methyleneterephthalate), poly(ethyleneterephthalate) and poly(butyleneterephthalate); epoxy resins; alkyds; phenolics; elastomers, for example, butadiene/styrene copolymers and butadiene/acrylonitrile copolymers; terpolymers of acrylonitrile, butadiene and styrene; natural rubber; butyl rubber; and polysiloxanes. The polymer may also be a blend of various polymers. The composition may contain any of the additives usually present and where appropriate to the particular polymers, may be crosslinked by chemical means or by irradiation.

It is a feature of the cured white bis-imides of this invention that their presence in a composition will not substantially contribute a yellow color or tint to an article formed from the composition by conventional molding techniques. For example, compositions containing white high impact polystyrene (HIPS) and from about 9 wt. % to about 15 wt. % cured white ethylene-bis-(tetrabromophthalimide), the latter having a Yellowness Index of about 10, can be used to produce molded articles having a Yellowness Index within the range of from about 16 to about 23. Also, in compositions containing from about 8 wt. % to about 14 wt. % of the same ethylene-bis-imide and white poly(butyleneterephthalate), a Yellowness Index within the range of from about 8 to about 13 is attainable.

The inventions disclosed herein are illustrated in the following Example.

The ethylene-bis-(phthalimide) reactant used in the Example was prepared in accordance with the following procedure.

A 5 liter resin kettle equipped with a stirrer, thermometer, condenser, Barret trap and heating mantle was charged with 1378 g of xylene and 590.5 g of acetic acid. The mixture was heated to 60° C. and stirred. Ethylene diamine (202.8 g) was dissolved in 200 g (234 cc) of xylene and kept separate. When the reaction temperature reached 60° C., phthalic anhydride was added to the kettle in ten increments of 100 g each, at ten minute intervals. The ethylene diamine/xylene solution was simultaneously added in ten increments of 42.55 cc each, at ten minute intervals. When the additions were complete, the reaction temperature was brought to 105° C. and then maintained within the range of 105° C. to 125° C. for a period of three hours. The reaction mass was cooled to room temperature and filtered. The filter cake was washed twice with xylene (500 cc each time) and 16 times with water (500 cc each time). The wet cake was dried at a temperature of 125° C. in a forced hot air oven overnight to give 1013g (94% yield) of ethylene-bis-(phthalimide) which was off-white in color and had a melting point of 239-241° C. and an acid value of 0.11

EXAMPLE I

For comparative purposes, yellow ethylene-bis-(tetrabromophthalimide), i.e. Ethyl Corporation's BT-93 ™ flame retardant, was obtained and uncured white ethylene-bis-(tetrabromophthalimide) and cured white ethylene-bis-tetrabromophthalimide) were prepared.

PREPARATION OF UNCURED WHITE ETHYLENE-BIS-(TETRABROMOPHTHALIMIDE)

A 3 liter resin kettle equipped with a stirrer, thermometer, thermowatch, double glycol condenser, addition funnel and heating mantle was charged with 1464 g of 65% oleum and 240.2 g of ethylene-bis-(phthalimide). The contents were stirred and heated to 55° C. Bromine (583 g) was then added dropwise over a period of five hours. After the addition was complete, the reaction mass was heated to reflux (60-63° C.) and maintained at that temperature for two hours. The reaction mass was further heated to 85° C. and stirred at that temperature for another eight hours. The unreacted bromine and $SO_3$ were distilled off. The reaction slurry was cooled to 30° C. and poured slowly over a large amount of ice. The product was washed with water eight times (3 liter of water each time) and then filtered. The filtered cake was dried at 125° C. overnight to give 683 g (96% yield) of the white ethylene-bis-(tetrabromophthalimide) with a melting point of 456-458° C.

PREPARATION OF CURED WHITE ETHYLENE-BIS-TETRABROMOPHTHALIMIDE)

White ethylene-bis-(tetrabromophthalimide) was prepared as above. Additionally, the following process step was performed. 643 g of previously dried (125° C.) white ethylene-bis-(tetrabromophthalimide) was placed as a thin layer, about ⅛ inch thick, on a sheet in a forced hot air oven. The material was then cured at a temperature of about 250° C. for 18 hours to yield 623 g of the material.

Thermogravimetric analyses were performed on the above produced yellow, uncured white and cured white ethylene-bis-(tetrabromophthalimide)s with a duPont 1090 Thermal Analyzer. Table I gives the results.

In the tables, EBT is defined as ethylene-bis-(tetrabromophthalimide).

TABLE I

| | TGA Results | | | | |
|---|---|---|---|---|---|
| | Weight % Remaining at Indicated Temperature | | | | |
| | 220° C. | 250° C. | 350° C. | 400° C. | 440° C. |
| Uncured white EBT | 99 | 98 | 93 | 90 | 82 |
| Cured white EBT | 100 | 100 | 99 | 97 | 90 |
| Yellow EBT | 100 | 100 | 99 | 98 | 92 |

Table II gives a % Br and acid number comparison between the uncured white and cured white ethylene-bis-(tetrabromophthalimide)s.

TABLE II

| | % Br | Acid No. |
|---|---|---|
| Uncured white EBT | 65.5 | 4.21 |
| Cured white EBT | 67.0 | 0.17 |

Uncured white and cured white ethylene-bis-(tetrabromophthalimide), the former having a Yellowness Index of about 5 to about 7 and the latter having a Yellowness Index of about 10 to about 14, were both compounded with white poly(butyleneterephthalate), i.e. VALOX 420, a product of the General Electric Company. The Yellowness Index was determined by a Hunter's Colorometer. The resultant composition was formulated as follows.

| Component | wt % |
|---|---|
| VALOX 325 | 85 |
| EBT | 10 |
| $Sb_2O_3$ | 5 |

The compounding was effected by use of a Brabender Mixer at a temperature of about 270° C.

The resultant composition was formed into plaques by compression molding. The compression molding press was operated at pressure of about 250 psi and at a temperature of about 230° C. with a molding time of 4 minutes. After the plaque was formed in the mold it was cooled to room temperature and then removed from the mold.

The plaques produced from the composition containing the uncured ethylene-bis-(tetrabromophthalimide) were noticeably yellower than the plaques produced from the composition containing the cured ethylene-bis-(tetrabromophthalimide), the latter being essentially yellow color free.

Table III compares the change in color of the plaques upon being exposed to ultraviolet light for 48 hours in a Sunlighter Model 150 manufactured by Test-Lab Apparatus Company of Milford, N.H.

TABLE III

| | Y.I. (Initial) | Y.I. (Final) | $\Delta E_{48}$ |
|---|---|---|---|
| Plaque containing uncured white EBT and VALOX 420 | 12.75 | 15.13 | 3.3 |
| Plaque containing cured white EBT and VALOX 420 | 11.03 | 13.13 | 2.0 |

Uncured white and cured white ethylene-bis-(tetrabromophthalimide) were compounded with white high impact polystyrene, HIPS 840D, a product of Huntsman Chemical Corp., to form a composition as follows:

| Component | wt % |
| --- | --- |
| HIPS 840D | 84 |
| EBT | 12 |
| Sb$_2$O$_3$ | 4 |

The compounding was accomplished with a Brabender Mixer at a temperature of about 175° C.

The composition was formed into plaques by compression molding in a compression molding press using a molding pressure of about 250 psi and at a temperature of about 180° C. with a molding time of about 3 minutes. After the plaque was compression molded, it was cooled to room temperature and then removed from the press.

The plaques containing uncured white ethylene-bis-(tetrabromophthalimide) were easily seen to have a yellow tint, while, in distinction, the plaques containing cured ethylene-bis-(tetrabromophthalimide) were not so colored.

Table IV compares the plaques after exposure to ultraviolet for 48 hours in the same apparatus used to obtain the values reported in Table III.

TABLE IV

| | Y.I. (Initial) | Y.I. (final) | ΔE$_{48}$ |
| --- | --- | --- | --- |
| Plaques containing uncured white EBT and HIPS 840D | 19.5 | 43.5 | 14.8 |
| Plaques containing cured white EBT and HIPS 840D | 16.7 | 22.6 | 4.6 |

What is claimed is:

1. A white product, predominantly consisting of a bis-imide selected from the group consisting of N,N'-ethylene-bis-(tetrabromophthalimide), N,N'-bis-(tetrabromophthalimide) or mixtures thereof, having an acid number of about 1.0 or less and a bromine content within the range of from about .63% to about 69%.

2. The white product of claim 1 wherein said bis-imide is N,N'-ethylene-bis-tetrabromophthalimide.

3. The white product of claim 2 wherein said acid number is within the range of from about 0.15 to about 1.0 and said bromine content is within the range of from about 65% to about 67%.

4. A white product, predominantly consisting of a bis-imide selected from the group consisting of N,N'-ethylene-bis-(tetrabromophthalimide), N,N'-bis-(tetrabromophthalimide) or mixtures thereof produced by bromination N,N'-bis-(phthalimide) or N,N'-bis-(phthalimide), as the case may be, with a brominating agent in the presence of oleum, which selected white product has after oven curing, an acid number of about 1.0 or less and a bromine content within the range of from about 63% to about 69%.

5. The white product of claim 4 wherein said bis-imide is N,N'-ethylene-bis-(tetrabromophthalimide).

6. The white product of claim 5 wherein said acid number is within the range of from about 0.15 to about 1.0 and said bromine content is within the range of from about 65% to about 67%.

7. A composition comprising a macromolecular flammable material and a bis-imide selected from the group consisting of white N,N'-ethylene-bis-)tetrabromophthalimide), and white N,N'-bis-tetrabromophthalimide) which has an acid number of about 1.0 or less and a bromine content within the range of from about 63% to about 69%.

8. The composition of claim 7 wherein said macromolecular material is a polymer.

9. The composition of claim 8 wherein said polymer is selected from the group consisting of polyolefins, polystyrenes, and polyesters.

10. The composition of claim 9 wherein the polymer is selected from the group consisting of cross-linked polyethylene, high impact polystyrene and poly(-butyleneterephthalate).

11. The composition of claim 8 wherein said bis-imide is N,N'-ethylene-bis-(tetrabromophthalimide).

12. The composition of claim 9 wherein said bis-imide is N,N'-ethylene-bis-(tetrabromophthalimide).

13. The composition of claim 10 wherein said bis-imide is N,N'-ethylene-bis-(tetrabromophthalimide).

14. A molded or extruded article formed from the composition of claim 8.

15. A molded or extruded article formed from the composition of claim 9.

16. A molded or extruded article formed from the composition of claim 10.

17. A composition comprising a macromolecular flammable material and a bis-imide selected from the group consisting of white N,N'-ethylene-bis-(tetrabromophthalimide), and white N,N'-bis-(tetrabromophthalimide) produced by brominating N,N'-ethylene-bis-(phthalimide) or N,N'-bis-(phthalimide), as the case may be, with a brominating agent in the presence of oleum, which selected bis-imide, has after oven curing, an acid number of about 1.0 or less and a bromine content within the range of from about 63% to about 69%.

18. The composition of claim 17 wherein said macromolecular material is a polymer.

19. The composition of claim 18 wherein said polymer is selected from the group consisting of polyolefins, polystyrenes, and polyesters.

20. The composition of claim 18 wherein the polymer is selected from the group consisting of cross-linked polyethylene, high impact polystyrene and poly(-butyleneterephthalate).

21. The composition of claim 18 wherein said bis-imide is N,N'-ethylene-bis-(tetrabromophthalimide).

22. The composition of claim 19 wherein said bis-imide is N,N'-ethylene-bis-(tetrabromophthalimide).

23. The composition of claim 20 wherein said bis-imide is N,N'-ethylene-bis-(tetrabromophthalimide).

24. A molded or extruded article formed from the composition of claim 18.

25. A molded or extruded article formed from the composition of claim 19.

26. A molded or extruded article formed from the composition of claim 20.

* * * * *